United States Patent
Quincy, III

(10) Patent No.: US 6,823,530 B2
(45) Date of Patent: Nov. 30, 2004

(54) ANTIMICROBIAL TREATMENT FOR SWIMWEAR

(75) Inventor: Roger Bradshaw Quincy, III, Cumming, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 289 days.

(21) Appl. No.: 09/929,673

(22) Filed: Aug. 14, 2001

(65) Prior Publication Data

US 2002/0077612 A1 Jun. 20, 2002

Related U.S. Application Data

(60) Provisional application No. 60/243,828, filed on Oct. 27, 2000.

(51) Int. Cl.$^7$ .................................................. A41D 5/00
(52) U.S. Cl. ........................... 2/67; 442/123; 442/124; 442/125; 442/417; 604/385.2; 604/396; 604/358
(58) Field of Search .............................. 2/67; 428/907; 442/123, 124, 125, 417; 604/358, 396, 385.2

(56) References Cited

U.S. PATENT DOCUMENTS

| | | |
|---|---|---|
| 3,338,992 A | 8/1967 | Kinney |
| 3,341,394 A | 9/1967 | Kinney |
| 3,502,538 A | 3/1970 | Petersen |
| 3,502,763 A | 3/1970 | Hartmann |
| 3,542,615 A | 11/1970 | Dobo et al. |
| 3,692,618 A | 9/1972 | Dorschner et al. |
| 3,802,817 A | 4/1974 | Matsuki et al. |
| 3,849,241 A | 11/1974 | Butin et al. |
| 4,340,563 A | 7/1982 | Appel et al. |
| 4,663,220 A | 5/1987 | Wisneski et al. |
| 4,940,464 A | 7/1990 | Van Gompel et al. |
| 5,046,272 A | 9/1991 | Vogt et al. |
| 5,104,116 A | 4/1992 | Pohjola |
| 5,224,405 A | 7/1993 | Pohjola |
| 5,226,992 A | 7/1993 | Morman |
| 5,490,983 A | 2/1996 | Worley et al. |
| 5,882,357 A * | 3/1999 | Sun et al. ................... 8/189 |
| 6,020,491 A | 2/2000 | Wonley et al. |
| 6,183,763 B1 | 2/2001 | Beerse et al. |
| 6,548,054 B2 | 4/2003 | Worley et al. |
| 2003/0044377 A1 | 3/2003 | Worley et al. |

FOREIGN PATENT DOCUMENTS

| | | |
|---|---|---|
| EP | 0 217 032 | 4/1987 |
| WO | WO 98/10648 | 3/1998 |
| WO | WO 00/29101 | 5/2000 |
| WO | WO 02/30477 A1 | 4/2002 |

* cited by examiner

*Primary Examiner*—Arti Singh
(74) *Attorney, Agent, or Firm*—Pauley Petersen & Erickson

(57) ABSTRACT

An absorbent swimwear garment having an antimicrobial agent based on hydantoin chemistry for the purpose of eliminating or reducing the level of bacteria in swim water. During initial product use, the absorbent swimwear garment is able to contain urine and bowel movements, similar to ordinary diapers and training pants. When the swimwear garment is submersed in swim water, particularly chlorinated or brominated water, the antimicrobial agent is stabilized and is thereby able to eliminate *E. coli* and other fecal bacteria from the swim water.

23 Claims, 3 Drawing Sheets

ANTIMICROBIAL TREATMENT FOR SWIMWEAR

This application claims the benefit of U.S. provisional No. 60/243,828 filed Oct. 27, 2000.

FIELD OF THE INVENTION

This invention is directed to swimpants and swimsuits for pre-toilet trained children. More particularly, the swimwear includes an antimicrobial treatment for treating bacteria in a swimming pool environment.

BACKGROUND OF THE INVENTION

Swim pants and swimsuits for pre-toilet trained children are designed to contain urine and bowel movements prior to swimming, similar to ordinary diapers and training pants. Even though the absorbent swimwear is designed to prevent leakage of urine and bowel movements out of the garment and seepage of swim water into the garment, swim water inevitably tends to make its way into the garment. The swim water inside the garment mixes with the urine and bowel movements inside the garment and may re-enter the swimming environment along with bacteria originating in the urine and bowel movements.

There is a need or desire for an absorbent swimwear garment that contains an agent that can eliminate or reduce the level of bacteria in swim water.

SUMMARY OF THE INVENTION

The present invention is directed to a pant-like absorbent swimwear garment, such as a swim pant or a swimsuit, that includes an antimicrobial agent that can be stabilized by chlorinated or brominated water. The antimicrobial agent can eliminate or reduce the level of bacteria in a swimming pool environment, particularly bacteria present as a result of fecal discharge. Escherichia coli (E. coli) is an example of one type of bacteria caused by fecal discharge.

Hydantoin and its derivatives can be used as antimicrobial agents. One particularly suitable hydantoin derivative is N-Halamine. An N-Halamine contains a halogen atom which can be effective at eliminating E. coli and other bacteria such as Proteus mirabilis (P. mirabilis). The N-Halamine can be obtained by exposing hydantoin (a 5-membered ring with nitrogen) to bleach (sodium hypochlorite) or other sources of chlorine or bromine. The hydantoin or its derivative can be applied to, or incorporated within, an absorbent swimwear garment, for example, via a modified polystyrene particle, or by grafting the antimicrobial agent onto pulp and then incorporating the grafted pulp into the swimwear garment, or by topically applying the hydantoin or its derivative to the swimwear garment. Exposure to chlorinated or brominated swim water then stabilizes the antimicrobial agent when the swimwear product is in use, i.e., being exposed to chlorinated or brominated swim water, thereby rendering the product effective for eliminating or reducing the level of bacteria that may occur from a bodily discharge.

With the foregoing in mind, it is a feature and advantage of the invention to provide an absorbent swimwear garment with an antimicrobial agent therein.

DEFINITIONS

Figure 1:
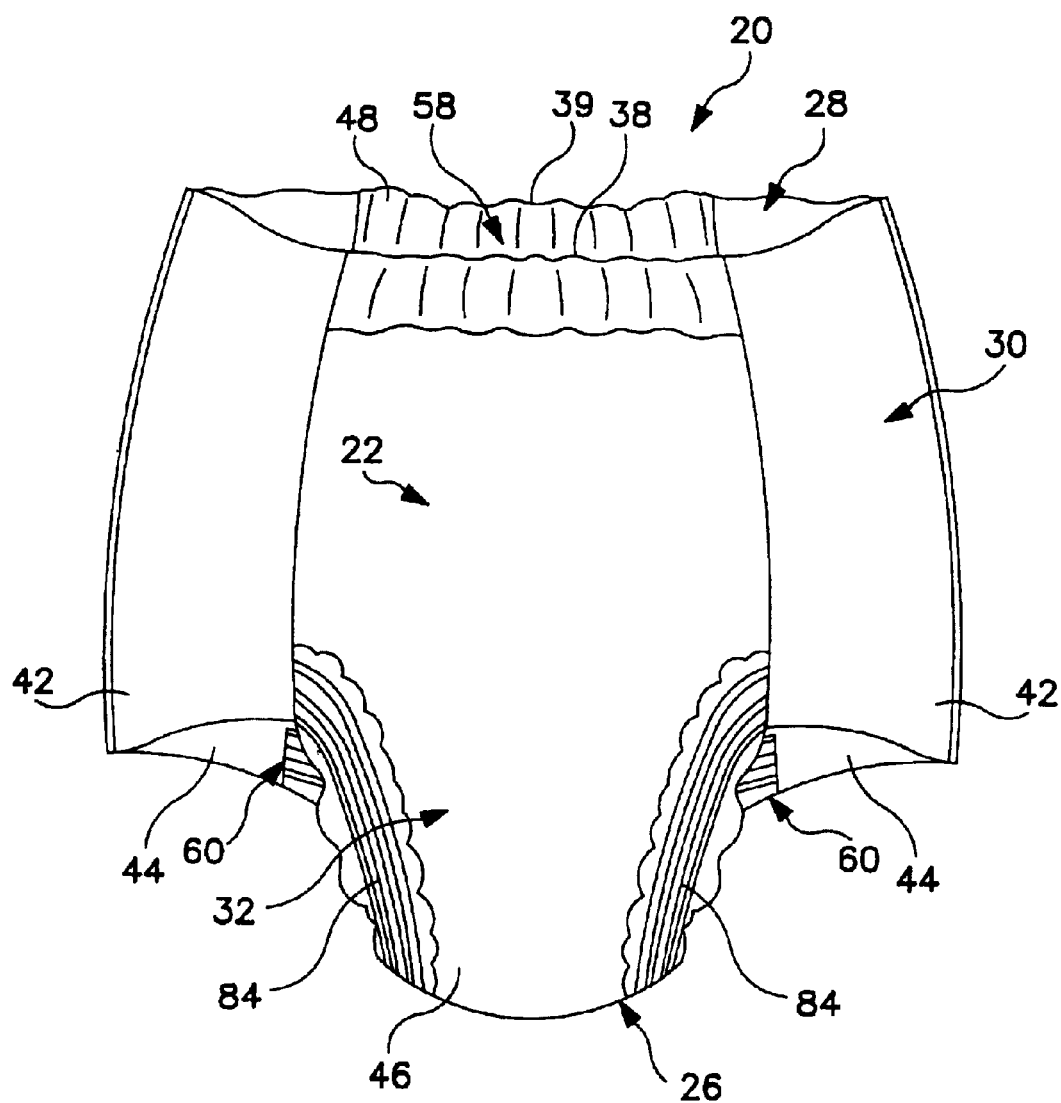
FIG. 1 is a front perspective view of an absorbent swimpant.

Within the context of this specification, each term or phrase below will include the following meaning or meanings.

"Applied to" refers to affixing, incorporating, attaching or integrating one element to another element. As used herein, the term "applied to" includes chemically attaching one element to another, chemically modifying one element with another, grafting one element onto another, integrating one element into a structure of another, as well as topically applying one element onto another.

"Attached to" refers to the joining, adhering, connecting, bonding, or the like, of two elements. Two elements will be considered to be attached to one another when they are attached directly to one another or indirectly to one another, such as when each is directly attached to intermediate elements.

"Elastic," "elasticized" and "elasticity" mean that property of a material or composite by virtue of which it tends to recover its original size and shape after removal of a force causing a deformation.

"Film" refers to a thermoplastic film made using a film extrusion and/or foaming process, such as a cast film or blown film extrusion process. The term includes apertured films, slit films, and other porous films which constitute liquid transfer films, as well as films which do not transfer liquid.

"Hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90° are designated "wettable" or hydrophilic, while fibers having contact angles greater than 90° are designated "non-wettable" or hydrophobic.

"Layer" when used in the singular can have the dual meaning of a single element or a plurality of elements.

"Liquid-impermeable," when used in describing a layer or multi-layer laminate, means that a liquid, such as urine, will not pass through the layer or laminate, under ordinary use conditions, in a direction generally perpendicular to the plane of the layer or laminate at the point of liquid contact. Liquid, or urine, may spread or be transported parallel to the plane of the liquid impermeable layer or laminate, but this is not considered to be within the meaning of "liquid-impermeable" when used herein.

"Liquid-permeable material" or "liquid water-permeable material" refers to a material present in one or more layers, such as a film, nonwoven fabric, or open-celled foam, which is porous, and which is water permeable due to the flow of water and other aqueous liquids through the pores. The pores in the film or foam, or spaces between fibers or filaments in a nonwoven web, are large enough and frequent enough to permit leakage and flow of liquid water through the material, but may be small enough to limit flow of liquid water only above a minimum hydrostatic pressure.

"Meltblown fibers" means fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. Meltblown fibers are microfibers which may be continuous or discontinuous, are generally smaller than about 0.6 denier, and are generally self-bonding when deposited onto a collecting surface. Meltblown fibers used in the present invention are preferably substantially continuous in length.

"Nonwoven" and "nonwoven web" refer to materials and webs of material which are formed without the aid of a textile weaving or knitting process.

"Polymers" include, but are not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to isotactic, syndiotactic and atactic symmetries.

"Pool water ingredient" refers to any substance added to a swimming pool or pond for treating the water, such as chlorine or bromine.

"Spunbonded fibers" refers to small diameter fibers which are formed by extruding molten thermoplastic material as filaments from a plurality of fine capillaries of a spinnerette having a circular or other configuration, with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Petersen, and U.S. Pat. No. 3,542,615 to Dobo et al., each of which is incorporated herein in its entirety by reference. Spunbond fibers are quenched and generally not tacky when they are deposited onto a collecting surface. Spunbond fibers are generally continuous and often have average deniers larger than about 0.3, more particularly, between about 0.6 and 10.

"Stabilize" refers to providing a conducive environment for an antimicrobial agent to maintain antimicrobial activity for an extended period of time.

"Superabsorbent" or "superabsorbent material" refers to a water-swellable, water-insoluble organic or inorganic material capable, under the most favorable conditions, of absorbing at least about 15 times its weight and, more desirably, at least about 25 times its weight in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds such as cross-linked polymers.

"Surface" includes any layer, film, woven, nonwoven, laminate, composite, or the like, whether pervious or impervious to air, gas, and/or liquids.

"Thermoplastic" describes a material that softens when exposed to heat and which substantially returns to a non-softened condition when cooled to room temperature.

These terms may be defined with additional language in the remaining portions of the specification.

DETAILED DESCRIPTION OF THE PRESENTLY PREFERRED EMBODIMENTS

The present invention is directed to an absorbent swimwear garment having an antimicrobial treatment for eliminating or reducing the level of bacteria in swim water, particularly in chlorinated or brominated pool water. The principles of the present invention can be incorporated into disposable, pant-like, absorbent swimwear articles, such as swimpants and swimsuits.

Figure 2:
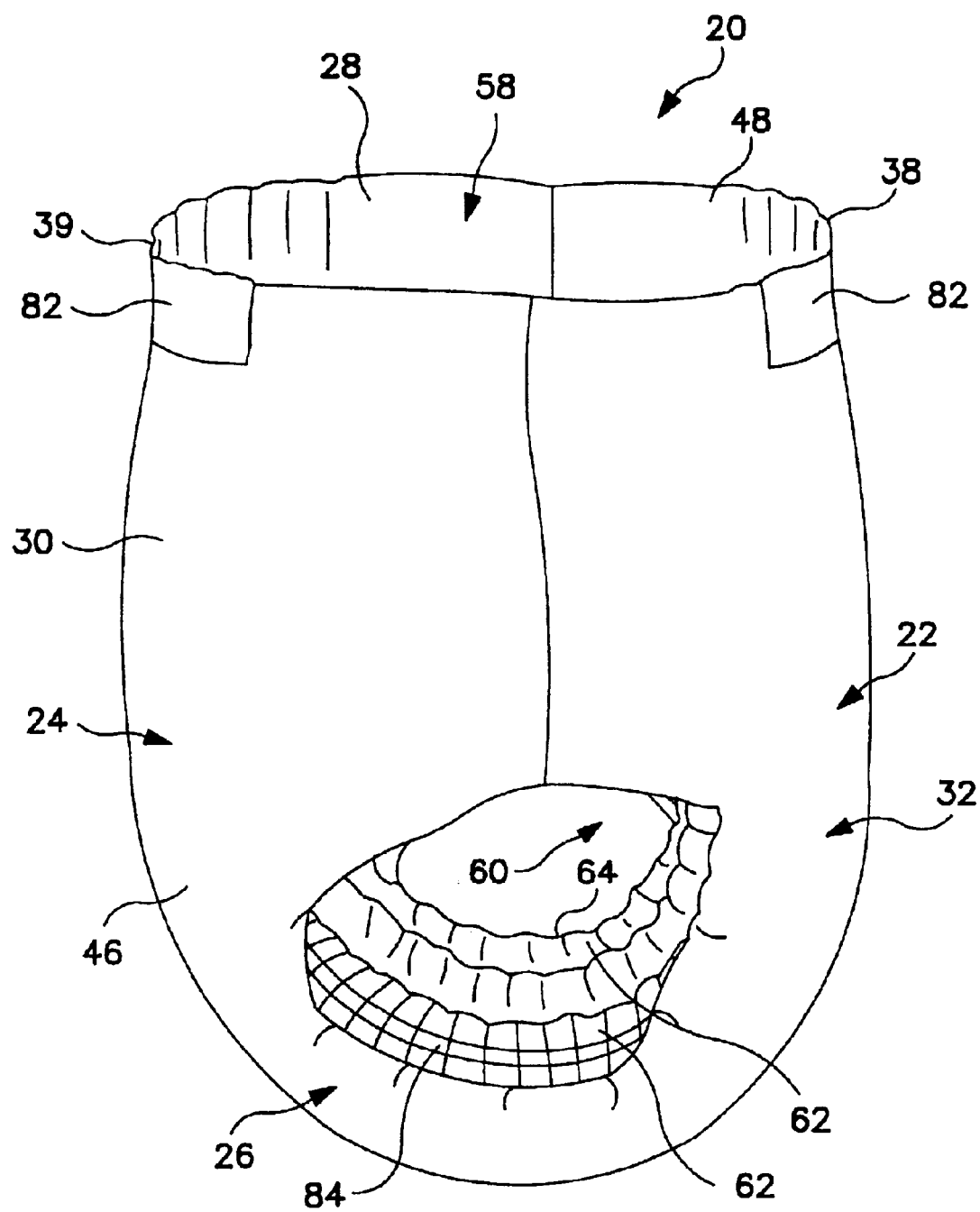
FIG. 2 is a side perspective view of an absorbent swimpant.

Referring to FIGS. 1 and 2, an absorbent swimpant 20 is illustrated. The swimpant 20 includes an absorbent chassis 32. The absorbent chassis 32 defines a front region 22, a back region 24, a crotch region 26 interconnecting the front and back regions, an inner surface 28 which is configured to contact the wearer, and an outer surface 30 opposite the inner surface which is configured to contact a pool environment.

Figure 3:
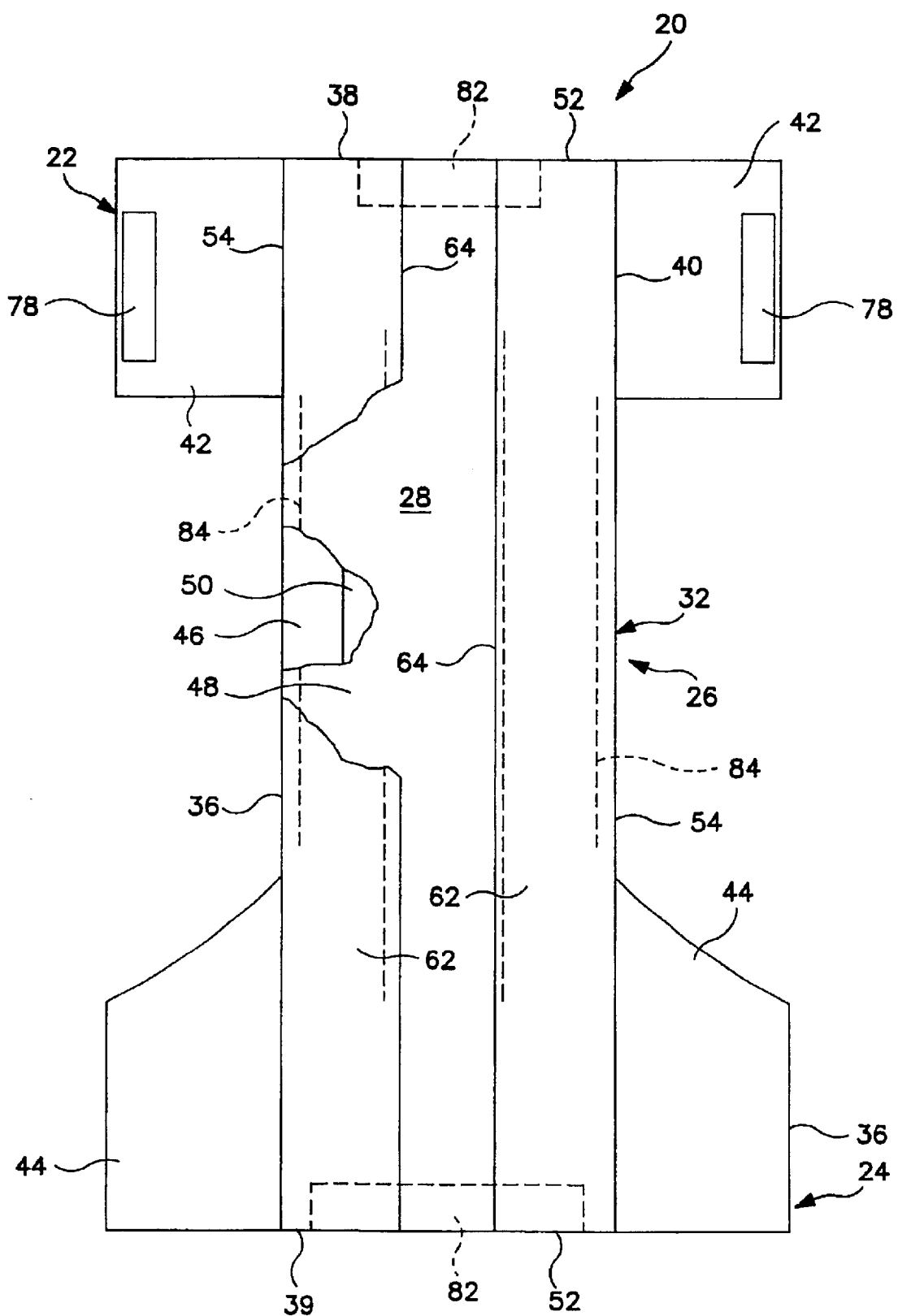
FIG. 3 is a plan view of an absorbent swimpant in a partially disassembled, stretched flat state, and showing the surface of the swimpant that faces the wearer when the swimpant is worn, and with portions cut away to show the underlying features.

Referring to FIG. 3, the swimpant 20 is shown in a partially disassembled, stretched flat state, showing the inner surface 28 which faces the wearer when the garment is worn. As shown, the absorbent chassis 32 also defines a pair of transversely opposed side edges 36 and a pair of longitudinally opposed waist edges, which are designated front waist edge 38 and back waist edge 39. The front region 22 is contiguous with the front waist edge 38, and the back region 24 is contiguous with the back waist edge 39. The chassis 32 also includes a somewhat rectangular composite structure 40, a pair of transversely opposed front side panels 42, and a pair of transversely opposed back side panels 44. The composite structure 40 and side panels 42 and 44 may be integrally formed, as shown in FIG. 2, or may include two or more separate elements, as shown in FIGS. 1 and 3.

The illustrated composite structure 40 includes an outer cover 46, a body side liner 48 which is connected to the outer cover 46 in a superposed relation, and an absorbent assembly 50 which is located between the outer cover 46 and the body side liner 48. The somewhat rectangular composite structure 40 has opposite linear end edges 52 that form portions of the front and back waist edges 38 and 39, and opposite linear, or curvilinear, side edges 54 that form portions of the side edges 36 of the absorbent chassis 32.

As shown in the swimpants 20 in FIGS. 1 and 2, the front and back regions 22 and 24 together define a three-dimensional pant configuration having a waist opening 58 and a pair of leg openings 60. The waist edges 38 and 39 of the absorbent chassis 32 are configured to encircle the waist of the wearer when worn and provide the waist opening 58 which defines a waist perimeter dimension. Portions of the transversely opposed side edges 36 (FIG. 3) in the crotch region 26 generally define the leg openings 60. The front region 22 includes the portion of the swimpant 20 which, when worn, is positioned on the front of the wearer while the back region 24 includes the portion of the swimpant 20 which, when worn, is positioned on the back of the wearer. The crotch region 26 of the swimpant 20 includes the portion of the swimpant 20 which, when worn, is positioned between the legs of the wearer and covers the lower torso of the wearer.

The absorbent chassis 32 is configured to contain and/or absorb any body exudates discharged from the wearer. For example, the absorbent chassis 32 can include a pair of elasticized containment flaps 62 (shown in FIGS. 2 and 3) which are configured to provide a barrier to the transverse flow of body exudates. More particularly, in terms of swimwear, the containment flaps 62 help prevent the escape of bowel movements from the swimpant 20. Furthermore, the containment flaps 62 provide pre-swim urine leakage protection when the absorbent assembly 50 can no longer acquire the incoming fluid at the rate at which it is being delivered.

The elasticized containment flaps 62 define an unattached edge 64 which assumes an upright, generally perpendicular configuration in at least the crotch region 26 of the swimpant 20 to form a seal against the wearer's body. Suitable constructions and arrangements for the containment flaps 62 are generally well known to those skilled in the art and are described in U.S. Pat. No. 4,704,116 issued Nov. 3, 1987 to Enloe, which is incorporated herein by reference.

Absorbent swimwear is designed for leakage prevention prior to swimming. When a wearer wears absorbent swimwear into a pool or lake, the swimwear has a tendency to fill up with water. The swim water that enters the swimwear mixes with the bodily excretions contained within the garment and may thereafter exit the garment, carrying with it bacteria from the bodily excretions. Solid waste is kept inside the swimpant 20 regardless of the release of the swim water, because the absorbent chassis 32 is constructed as in a normal absorbent garment, such as a diaper or training pant, to keep bowel movements contained therein. Nevertheless, bacteria can still be carried outside the garment 20 by the water. Therefore, the swimpant 20 of this invention is equipped with an antimicrobial agent to eliminate or reduce the level of bacteria that would otherwise be present in the swim water. The action of the antimicrobial agent may be effective prior to, concurrent with and/or subsequent to the release of any swim water from the swimpant 20.

The antimicrobial agent can be hydantoin or a hydantoin derivative. N-Halamines are a general category of heterocyclic ring compounds derived from hydantoins. An N-Halamine contains a halogen atom in the structure, which has been shown to be very effective at eliminating *E. coli* and other bacteria, such as *Proteus mirabilis*. The N-Halamine can be obtained by exposing a hydantoin (a 5-membered ring with nitrogen) to bleach (sodium hypochlorite) or other source of halogen, suitably chlorine or bromine, thereby "activating" the N-Halamine. The antimicrobial agent can include the "activated" N-Halamine which can be stabilized through exposure to dilute halogens, such as through exposure to chlorinated or brominated swim water while a wearer is in a swimming pool. More specifically, the swim water provides an additional source of free halogen atoms which help maintain the activated state of the activated N-Halamine for an extended period of time, thereby maintaining the antimicrobial activity of the antimicrobial agent for an extended period of time. One product source of N-Halamine pre-cursor chemicals, namely hydantoin and hydantoin derivatives, is HaloSource Corporation in Seattle, Wash. An example of a suitable hydantoin is polystyrene hydantoin, having the general formula $(C_{12}H_{12}N_2O_2)_n$, which is available from HaloSource Corporation. This particular hydantoin can be halogenated, thereby resulting in the general formula $(C_{12}H_{10}X_2N_2O_2)_n$, where X can be either Cl or Br. Hydantoin derivatives are effective for treating *Escherichia coli* (*E. coli*) and other fecal associated bacteria.

The antimicrobial agent can be applied to the garment 20 in several different ways. For example, the antimicrobial agent can be attached to a surface of a non-porous material in the garment 20, such as the surface of a film or a dissolvable material. Alternatively, the antimicrobial agent can be incorporated within a porous material in the garment 20, such as within a nonwoven web in the body side liner 48. In yet another alternative, the antimicrobial agent can be topically applied to virtually any component of the garment 20. Suitable materials for the various components of the garment 20 are described in greater detail below.

An example of a suitable hydantoin derivative that can be topically applied to the garment 20 is DMDM (dimethyl dimethyl) Hydantoin, available from McIntyre Group, Ltd., of Park Forest, Ill., under the tradename MACKSTAT® DM. DMDM Hydantoin is compatible with anionic, cationic, nonionic, and amphoteric surfactants, as well as with proteins, aloe, cationic and nonionic polymers, amines, and more, and thus can be applied topically to a wide variety of materials, including generally each of the components of the garment 20 of the invention. DMDM Hydantoin is highly effective against gram negative and positive bacteria. Furthermore, DMDM Hydantoin is stable over a wide pH range and does not break down if held above room temperature (50° Celsius) for a long period of time. DMDM Hydantoin has the following formula:

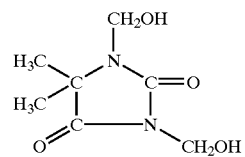

Another specific method of applying the antimicrobial agent to the garment 20 includes treating pulp, or cotton-containing fabric, with cyclic hydantoins, which graft onto the cellulose backbone of the fiber. Coform is a particularly suitable fabric for such treatment. The fabric is then treated with chlorine bleach, converting the hydantoin moiety into a halamine by replacing one hydrogen atom with one chlorine atom, as shown:

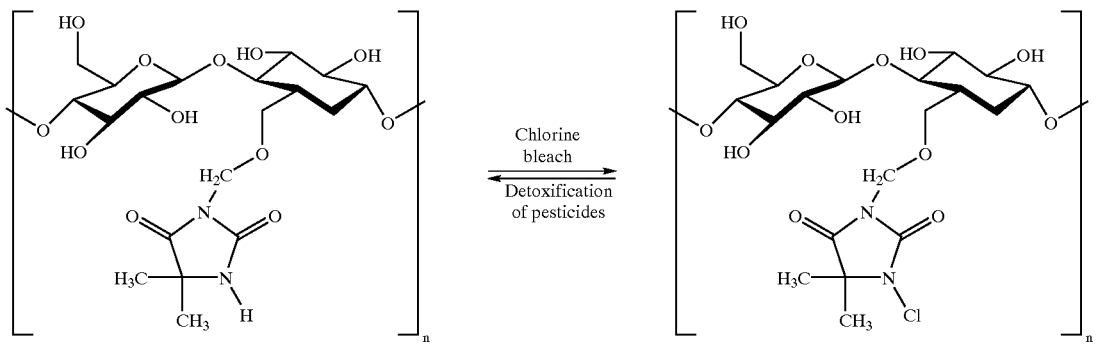

Yet another specific method of applying the antimicrobial agent to the garment 20 includes covalently linking an activated N-Halamine compound onto cellulose. Once again, coform is a particularly suitable fabric for such treatment.

It may also be possible to co-extrude the antimicrobial agent with one or more components of the garment 20.

As mentioned, the antimicrobial agent can be applied to any one or more of the components of the swimpant 20, including the body side liner 48, the outer cover 46, the absorbent assembly 50, the containment flaps 62, and/or a separate layer (not shown) attached to the swimpant 20 solely or primarily to deliver the antimicrobial agent. The antimicrobial agent can be grafted to pulp in cellulose fibers of coform within the absorbent assembly 50, or added to the coform or other materials within the swimpant 20 in the form of modified polystyrene particles such as polystyrene hydantoin, or can be applied topically to the garment 20 in the form of DMDM Hydantoin, for example. Since the swim water may leak into and out of the swimpant 20 through the waist opening 58 and the leg openings 60, the areas of the swimpant 20 around the waist opening 58 and around the leg openings 60 are quite suitable for placement of the antimicrobial agent. The inclusion of containment flaps 62 reduces such leakage.

The inner surface 28 of the body side liner 48 is a particularly suitable location for the antimicrobial agent. With the antimicrobial agent in direct contact with, or in close proximity to, any contained fecal discharges, the hydantoin derivative can easily interact with any bacteria present in the fecal discharge and can be stabilized by any chlorinated or brominated swim water that seeps into the swimpant 20.

The outer surface 30 of the outer cover 46 is another particularly suitable location for the antimicrobial agent. By applying the antimicrobial agent to the outer surface 30 of the outer cover 46, the antimicrobial agent is released to the aqueous environment. Once in the aqueous environment, the hydantoin derivative interacts with the chlorine or bromine and the bacteria in a limited zone in and around the swimpant 20. This embodiment is effective for short-term use, since, over time, the bactericidal capabilities are reduced by migration of the antimicrobial agent out of and away from the swimpant 20, thus decreasing the effective concentration of the antimicrobial agent.

The absorbent assembly 50, positioned between the outer cover 46 and the body side liner 48, can be any structure which is generally compressible, conformable, non-irritating to the child's skin, and capable of absorbing and retaining liquids and certain body wastes. The absorbent assembly 50 can be manufactured in a wide variety of sizes and shapes, and from a wide variety of liquid absorbent materials commonly used in the art. For example, the absorbent assembly 50 can suitably include a matrix of hydrophilic fibers, such as a web of cellulosic fluff, mixed with particles of a high-absorbency material commonly known as superabsorbent material. In a particular embodiment, the absorbent assembly 50 includes a matrix of cellulosic fluff, such as wood pulp fluff, and superabsorbent hydrogel-forming particles. The wood pulp fluff can be exchanged with synthetic, polymeric, meltblown fibers or with a combination of meltblown fibers and natural fibers. The superabsorbent particles can be substantially homogeneously mixed with the hydrophilic fibers or can be nonuniformly mixed. The fluff and superabsorbent particles can also be selectively placed into desired zones of the absorbent assembly 50 to better contain and absorb body exudates. The concentration of the superabsorbent particles can also vary through the thickness of the absorbent assembly 50. Alternatively, the absorbent assembly 50 can include a laminate of fibrous webs and superabsorbent material or other suitable means of maintaining a superabsorbent material in a localized area. Another type of absorbent material suitable for the absorbent assembly 50 is coform, which is a blend of staple length pulp fibers and melt-blown fibers. The weight ratio of staple fibers to melt-blown fibers may range between 30 (staple)/70 (melt-blown) and 90 (staple)/10 (melt-blown). Wood pulp fibers are preferred for the staple fibers and polypropylene is preferred for the melt-blown fibers. Superabsorbent materials may be added to the coform to increase fluid absorption capacity.

Suitable superabsorbent materials can be selected from natural, synthetic, and modified natural polymers and materials. The superabsorbent materials can be inorganic materials, such as silica gels, or organic compounds, such as crosslinked polymers. Suitable superabsorbent materials are available from various commercial vendors, such as Dow Chemical Company located in Midland, Mich., U.S.A., and Stockhausen GmbH & Co. KG, D-47805 Krefeld, Federal Republic of Germany. Typically, a superabsorbent material is capable of absorbing at least about 15 times its weight in water, and desirably is capable of absorbing more than about 25 times its weight in water.

In one embodiment, the absorbent assembly 50 is generally rectangular in shape, and includes a blend of wood pulp fluff and superabsorbent material. One preferred type of fluff is identified with the trade designation CR1654, available from U.S. Alliance, Childersburg, Ala., U.S.A., and is a bleached, highly absorbent sulfate wood pulp containing primarily soft wood fibers. As a general rule, the superabsorbent material is present in the absorbent assembly 50 in an amount of from about 0 to about 90 weight percent based on total weight of the absorbent assembly 50. The absorbent assembly 50 suitably has a density within the range of about 0.10 to about 0.35 grams per cubic centimeter. The absorbent assembly 50 may or may not be wrapped or encompassed by a suitable tissue wrap that maintains the integrity and/or shape of the absorbent assembly 50.

The absorbent chassis 32 can also incorporate other materials that are designed primarily to receive, temporarily store, and/or transport liquid along the mutually facing surface with the absorbent assembly 50, thereby maximizing the absorbent capacity of the absorbent assembly 50. One suitable material is referred to as a surge layer (not shown) and includes a material having a basis weight of about 50 to about 120 grams per square meter, and including a through-air-bonded-carded web of a homogenous blend of 60 percent 3 denier type T-256 bicomponent fiber including a polyester core/polyethylene sheath and 40 percent 6 denier type T-295 polyester fiber, both commercially available from Kosa Corporation of Salisbury, N.C., U.S.A.

The outer cover 46 desirably includes a material that is substantially liquid impermeable, and can be elastic, stretchable or nonstretchable. The outer cover 46 can be a single layer of liquid impermeable material, but desirably includes a multi-layered laminate structure in which at least one of the layers is liquid impermeable. For instance, the outer cover 46 can include a liquid permeable outer layer and a liquid impermeable inner layer that are suitably joined together by a laminate adhesive (not shown). Suitable laminate adhesives, which can be applied continuously or intermittently as beads, a spray, parallel swirls, or the like, can be obtained from Findley Adhesives, Inc., of Wauwatosa, Wis., U.S.A., or from National Starch and Chemical Company, Bridgewater, N.J., U.S.A. The liquid permeable outer layer can be any suitable material and desirably one that provides a generally cloth-like texture. One example of such a material is a 20 gsm (grams per square meter) spunbond polypropylene nonwoven web. The outer layer may also be made of those materials of which the liquid permeable body side liner 48 is made. While it is not a necessity for the outer layer to be liquid permeable, it is desired that it provides a relatively cloth-like texture to the wearer.

The inner layer of the outer cover 46 can be both liquid and vapor impermeable, or can be liquid impermeable and vapor permeable. The inner layer is desirably manufactured from a thin plastic film, although other flexible liquid impermeable materials may also be used. The inner layer, or the liquid impermeable outer cover 46 when a single layer, prevents waste material from wetting articles, such as car seats and clothing, as well as the wearer and care giver. A suitable liquid impermeable film for use as a liquid impermeable inner layer, or a single layer liquid impermeable outer cover 46, is a 0.2 millimeter polyethylene film commercially available from Huntsman Packaging of Newport News, Va., U.S.A. If the outer cover 46 is a single layer of material, it can be embossed and/or matte finished to provide a more cloth-like appearance. As earlier mentioned, the liquid impermeable material can permit vapors to escape from the interior of the disposable absorbent article, while still preventing liquids from passing through the outer cover 46. A suitable "breathable" material is composed of a microporous polymer film or a nonwoven fabric that has been coated or otherwise treated to impart a desired level of liquid impermeability. A suitable microporous film is a PMP-1 film material commercially available from Mitsui Toatsu Chemicals, Inc., Tokyo, Japan, or an XKO-8044 polyolefin film commercially available from 3M Company. Minneapolis, Minn.

The liquid permeable body side liner 48 is illustrated as overlying the outer cover 46 and absorbent assembly 50 (FIG. 3), and may but need not have the same dimensions as the outer cover 46. The body side liner 48 is desirably compliant, soft feeling, and non-irritating to the child's skin. Further, the body side liner 48 can be less hydrophilic than the absorbent assembly 50, to present a relatively dry surface to the wearer and permit liquid to readily penetrate through its thickness.

The body side liner 48 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the body side liner 48. For example, the body side liner 48 can be composed of a meltblown or spunbonded web of polyolefin fibers. The body side liner 48 can also be a bonded-carded web composed of natural and/or synthetic fibers. The body side liner 48 can be composed of a substantially hydrophobic material, and the hydrophobic material can, optionally, be treated with a surfactant or otherwise processed to impart a desired level of wettability and hydrophilicity. For example, the material can be surface treated with about 0.28 weight percent of a surfactant commercially available from the Rohm and Haas Co. under the trade designation Triton X-102. The surfactant can be applied by any conventional means, such as spraying, printing, brush coating or the like. The surfactant can be applied to the entire body side liner 48 or can be selectively applied to particular sections of the body side liner, such as the medial section along the longitudinal centerline.

A suitable liquid permeable body side liner 48 is a nonwoven bicomponent web having a basis weight of about 27 gsm. The nonwoven bicomponent can be a spunbond bicomponent web, or a bonded carded bicomponent web. Suitable bicomponent staple fibers include a polyethylene/polypropylene bicomponent fiber available from CHISSO Corporation, Osaka, Japan. In this particular bicomponent fiber, the polypropylene forms the core and the polyethylene forms the sheath of the fiber. Other fiber orientations are possible, such as multi-lobe, side-by-side, end-to-end, or the like. While the outer cover 46 and body side liner 48 can include elastomeric materials, it can be desirable in some embodiments for the composite structure to be generally inelastic, where the outer cover 46, the body side liner 48 and the absorbent assembly 50 include materials that are generally not elastomeric.

The containment flaps 62 may be made of those materials of which the outer cover 46 and/or the body side liner 48 is made.

As noted previously, the illustrated swimpant 20 can have front and back side panels 42 and 44 disposed on each side of the absorbent chassis 32 (FIGS. 1 and 3). These transversely opposed front side panels 42 and transversely opposed back side panels 44 can be permanently bonded to the composite structure 40 of the absorbent chassis 32 and can be permanently bonded to one another along corresponding sides. Alternatively, the front and back side panels 42, 44 can be releasably attached to one another by a fastening system 78 (FIG. 3). The side panels 42 and 44 may be attached to the composite structure 40 and/or to one another using attachment means known to those skilled in the art such as adhesive, thermal or ultrasonic bonding. The side panels 42 and 44 can also be formed as a portion of a component of the composite structure 40, such as the outer cover 46 or the body side liner 48.

Suitable elastic materials, as well as one described process of incorporating elastic side panels into an absorbent garment, are described in the following U.S. Pat. No. 4,940,464 issued Jul. 10, 1990 to Van Gompel et al.; U.S. Pat. No. 5,224,405 issued Jul. 6, 1993 to Pohjola; U.S. Pat. No. 5,104,116 issued Apr. 14, 1992 to Pohjola; and U.S. Pat. No. 5,046,272 issued Sep. 10, 1991 to Vogt et al.; all of which are incorporated herein by reference. In particular embodiments, the elastic material includes a stretch-thermal laminate (STL), a neck-bonded laminated (BL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Morman; and European Patent Application No. EP 0 217 032 published on Apr. 8, 1987 in the names of Taylor et al.; all of which are incorporated herein by reference. Alternatively, the side panel material may include other woven or nonwoven materials, such as those described above as being suitable for the outer cover 46 or body side liner 48, or stretchable but inelastic materials.

To further enhance containment and/or absorption of body exudates, the swimpant 20 can include waist elastic members 82 and/or leg elastic members 84, as are known to those skilled in the art (FIGS. 1–3). The waist elastic members 82 can be operatively joined to the outer cover 46 and/or to the body side liner 48, and can extend over part or all of the waist edges 38, 39. The leg elastic members 84 are desirably operatively joined to the outer cover 46 and/or to the body side liner 48 longitudinally along the opposite side edges 36 and positioned in the crotch region 26 of the swimpant 20.

The waist elastic members 82 and the leg elastic members 84 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat; such that elastic constrictive forces are imparted to the substrate. In one particular embodiment, for example, the waist elastic members 82 and/or the leg elastic members 84 include a plurality of dry-spun coalesced multifilament spandex elastomeric threads sold under the trade name LYCRA® and available from E. I. du Pont de Nemours and Company, Wilmington, Del., U.S.A. In another particular embodiment, for example, the waist elastic members 82 and/or the leg elastic members 84 include Findley HX 2695-01 adhesive laminated to two facings of 0.6 osy bicomponent polypropylene/polyethylene spunbond. Alternatively, six strands of 310 decitex LYCRA® may be also laminated at 250% elongation between the spunbond facings in addition to the Findley adhesive.

As described herein, the various components of the swimpant 20 can be integrally assembled together employing various types of suitable attachment means, such as adhesive, sonic and thermal bonds or combinations thereof. The resulting product is an absorbent swimwear garment 20 that provides uncompromised urine and bowel movement containment before swimming, and includes an antimicrobial treatment for eliminating or reducing the level of bacteria in swim water. Furthermore, the antimicrobial treatment can be stabilized through exposure to chlorinated or brominated pool water.

EXAMPLE

In this example, polystyrene hydantoin (PSH) particles from HaloSource Corporation were incorporated into the cellulose (pulp) component of a 160 gsm coform (70% pulp/30% polypropylene fabric). It was estimated that the fabric contained about 10 gsm (6 wt %) PSH. A surfactant, AHCOVEL® Base N-62 from Hodgson Chemical Co., was topically applied to the surface of the fabric to provide wettability to aqueous-based fluids. It was estimated that the fabric contained about 0.5 wt % AHCOVEL® surfactant. The PSH was then converted into N-Halamine by exposing the fabric to a bleach solution. The bleach removed the surfactant treatment. Therefore, the AHCOVEL® surfactant was reapplied to the surface of the fabric at an estimated level of 0.5 wt %. The N-Halamine + AHCOVEL®-treated fabric was then tested for antimicrobial properties. A modified AATCC Method 100 that included independent testing with *S. aureus*, *E. coli*, and *P. mirabilis* bacteria was used. A culture medium (Tryptic Soy Agar) was inoculated with the organism and 1 mL of the inoculum was then applied to a 4.8 cm diameter circular piece of the fabric. The neutralizer solution was Letheen Broth. The organism population (colony forming units (cfu) per mL) was determined at initial contact time and after a 4-hour contact time at 35–39° Celsius. Table 1 shows the results for a first fabric piece and Table 2 shows the results for a second fabric piece, both of which were treated in the manner described in this example.

TABLE 1

Fabric Sample #1

| Test Sample and Organism | S. aureus ATCC 6538 | E. coli ATCC 8739 | P. mirabilis ATCC 4630 |
|---|---|---|---|
| Inoculum Concentration | $1.5 \times 10^9$ cfu/mL | $3.3 \times 10^8$ cfu/mL | $3.6 \times 10^8$ cfu/mL |
| Initial Contact Time | $4.8 \times 10^6$ cfu/mL | $1.6 \times 10^6$ cfu/mL | $2.1 \times 10^6$ cfu/mL |
| 4-Hour Contact Time | $<1 \times 10^2$ cfu/mL | $5.0 \times 10^2$ cfu/mL | $<1 \times 10^2$ cfu/mL |
| Percent Reduction | 99.99% | 99.97% | 99.99% |

TABLE 2

Fabric Sample #2

| Test Sample and Organism | S. aureus ATCC 6538 | E. coli ATCC 8739 | P. mirabilis ATCC 4630 |
|---|---|---|---|
| Inoculum Concentration | $1.5 \times 10^9$ cfu/mL | $3.3 \times 10^8$ cfu/mL | $3.6 \times 10^8$ cfu/mL |
| Initial Contact Time | $7.0 \times 10^6$ cfu/mL | $1.7 \times 10^6$ cfu/mL | $2.1 \times 10^6$ cfu/mL |
| 4-Hour Contact Time | $<1 \times 10^2$ cfu/mL | $<1 \times 10^2$ cfu/mL | $<1 \times 10^2$ cfu/mL |
| Percent Reduction | 99.99% | 99.99% | 99.99% |

From this example, it is evident that the N-Halamine chemistry is effective at eliminating bacteria. This antimicrobial agent is ideal for absorbent swimwear garments which are exposed to chlorinated or brominated water when used in a swimming pool. The chlorinated or brominated water should stabilize the antimicrobial agent to make the swimwear garment effective for eliminating or reducing the level of bacteria that may occur from a fecal discharge.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

What is claimed is:

1. A disposable swimwear garment comprising:

a chassis including an outer cover, a body side liner, and an absorbent assembly between the outer cover and the body side liner, the chassis defining a waist opening and first and second leg openings; and an antimicrobial agent, including a hydantoin derivative, applied to the disposable swimwear garment.

2. The swimwear garment of claim 1, wherein the antimicrobial agent is applied to the outer cover.

3. The swimwear garment of claim 1, wherein the antimicrobial agent is applied to the body side liner.

4. The swimwear garment of claim 1, further comprising a pair containment flaps adjacent the leg openings of the chassis.

5. The swimwear garment of claim 4 wherein the antimicrobial agent is applied to the containment flaps.

6. The swimwear garment of claim 1, wherein the antimicrobial agent is applied to the garment via a modified polystyrene particle.

7. The swimwear garment of claim 1, wherein the antimicrobial agent comprises an N-Halamine.

8. The swimwear garment of claim 1, wherein the antimicrobial agent comprises dimethyl dimethyl hydantoin.

9. The swimwear garment of claim 1, wherein the antimicrobial agent comprises polystyrene hydantoin.

10. The swimwear garment of claim 1, wherein the antimicrobial agent comprises chlorinated polystyrene hydantoin.

11. The swimwear garment of claim 1, wherein the swimwear garment is intended for use in chlorinated water.

12. The swimwear garment of claim 1, wherein the swimwear garment is intended for use in brominated water.

13. The swimwear garment of claim 1, wherein the chassis comprises a porous, nonwoven web, and the antimicrobial agent is applied to the nonwoven web.

14. The swimwear garment of claim 1, wherein the chassis comprises a non-porous material, and the antimicrobial agent is applied to a surface of the non-porous material.

15. A disposable swimwear garment comprising:

a chassis including an outer cover, a body side liner, and an absorbent assembly between the outer cover and the body side liner, the chassis defining a waist opening and first and second leg openings; and an antimicrobial agent, including a hydantoin derivative, applied to the absorbent assembly.

16. The swimwear garment of claim 15, wherein the antimicrobial agent is grafted onto pulp and the grafted pulp is incorporated into the absorbent assembly.

17. The swimwear garment of claim 15, wherein the antimicrobial agent is applied to the absorbent assembly via a modified polystyrene particle.

18. The swimwear garment of claim 15, wherein the antimicrobial agent comprises an N-Halamine.

19. The swimwear garment of claim 15, wherein the antimicrobial agent comprises dimethyl dimethyl hydantoin.

20. The swimwear garment of claim 15, wherein the antimicrobial agent comprises polystyrene hydantoin.

21. The swimwear garment of claim 15, wherein the antimicrobial agent comprises chlorinated polystyrene hydantoin.

22. The swimwear garment of claim 15, wherein the swimwear garment is intended for use in chlorinated water.

23. The swimwear garment of claim 15, wherein the swimwear garment is intended for use in brominated water.

* * * * *